United States Patent [19]
Philipp et al.

[11] 3,978,066
[45] Aug. 31, 1976

[54] CERTAIN 4,6-DIHYDROPYRROLOTRIAZOLINE-QUINOLINE DERIVATIVES

[75] Inventors: Adolf H. Philipp; Christopher A. Demerson, both of Montreal; Leslie G. Humber, Dollard des Ormeaux, all of Canada

[73] Assignee: Ayerst, McKenna and Harrison Ltd., Montreal, Canada

[22] Filed: May 19, 1975

[21] Appl. No.: 578,599

Related U.S. Application Data

[62] Division of Ser. No. 413,418, Nov. 6, 1973, Pat. No. 3,900,477.

[52] U.S. Cl. ............................ 260/288 CF; 424/258
[51] Int. Cl.² ...................................... C07D 471/16
[58] Field of Search ............................... 260/258 CF

[56] References Cited
UNITED STATES PATENTS

| | | | |
|---|---|---|---|
| 3,272,804 | 9/1966 | Archer et al. | 260/288 CF |
| 3,833,591 | 9/1974 | McManus | 260/288 CF |
| 3,900,477 | 8/1975 | Philipp et al. | 260/288 CF |

OTHER PUBLICATIONS

Horning et al; Can. J. Chem. 49, pp. 2797–2802 (1971).

*Primary Examiner*—Nicholas S. Rizzo
*Assistant Examiner*—Mary C. Vaughn

[57] ABSTRACT

1,3-Dihydropyrrolo[4,3,2-de]isoquinoline derivatives characterized by an amino or hydrazino substituent at position 5 are disclosed. Also included are the related 4,6-dihydropyrrolo[4,3,2-de]-s-triazolo[3,4-a]isoquinoline and its 8-methyl derivative. The compounds are antidepressant and antihypertensive agents. Methods for their preparation and use are disclosed.

3 Claims, No Drawings

CERTAIN 4,6-DIHYDROPYRROLOTRIAZOLINE-QUINOLINE DERIVATIVES

This is a division of application Ser. No. 413,418, filed Nov. 6, 1973, now U.S. Pat. No. 3,900,477, issued Aug. 19, 1975.

BACKGROUND OF THE INVENTION

1. Field of Invention

This invention relates to pyrroloisoquinoline and pyrrolotriazoloisoquinoline derivatives, to intermediates used in their preparation and to methods for preparing and using these compounds.

More specifically, this invention relates to pyrrolo[4,3,2-de]isoquinolines and pyrrolotriazoloisoquinolines possessing central nervous system and circulatory system activities. For example, the compounds of this invention show antidepressant and antihypertensive properties in mammals at dose levels which do not elicit undesirable side effects. This combination of attributes render the pyrroloisoquinoline derivatives of the invention useful and desirable as therapeutic agents.

2. Prior Art

Prior interest in the field of pyrroloisoquinolines seems to be practically nonexistent. The only reference to this unusual ring system appears to be a recent chemical paper, D. E. Horning, et al., Can. J. Chem., 49, 2797 (1971), in which the main object of the paper was the preparation of particular 2-substituted 4-indolecarboxylic acids, a 1,3,4,5-tetrahydropyrrolo[4,3,2-de]isoquinolin-5-one intermediate being isolated in the process.

On the other hand some interest has been shown for the related field of pyrroloquinolines and 1H-azepino[4,3,2-cd]indoles. For example, see J. B Hester, J. Org. Chem. 29, 1158 (1964) and 32, 4095 (1967); see also U.S. Pat. No. 3,330,835, issued July 11, 1967 and U.S. Pat. No. 3,314,942, issued Apr. 18, 1967. However, the compounds of the present invention are distinguished from these prior art compounds by their different ring structure, nature of substituents, degrees of unsaturation and pharmacologic properties.

The pyrrolotriazoloisoquinolines of this invention are based on a novel tetracyclic ring system. The closest prior art to these compounds would appear to be the reference noted above.

SUMMARY OF THE INVENTION

The pyrroloisoquinolines of this invention are represented by formula 1

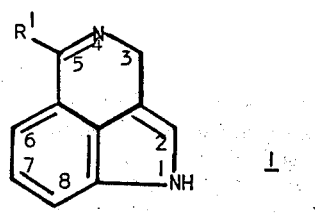

in which $R^1$ is amino, lower alkylamino, di(lower)alkylamino, di(lower)alkylamino(lower)alkylamino in which the alkylene portion thereof contains two to six carbon atoms, hydrazino, 2-(lower)alkylhydrazino, 2,2-di(lower)alkylhydrazino and isopropylidenehydrazino.

The pyrrolotriazoloisoquinolines of this invention are represented by formula 1a

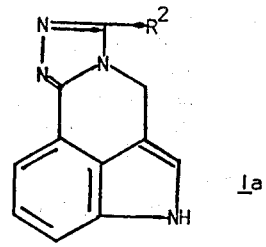

in which $R^2$ is hydrogen or methyl.

DETAILED DESCRIPTION OF THE INVENTION

The term "lower alkyl" as used herein contemplates straight chain alkyl radicals containing from one to six carbon atoms and branched chain alkyl radicals containing from three to four carbon atoms and includes methyl, ethyl, propyl, isopropyl, butyl, isobutyl, pentyl and the like.

The compounds of formulae 1 and 1a are capable of forming acid addition salts with pharmaceutically acceptable acids. Such acid addition salts are included within the scope of this invention. These salts, when administered to mammals, possess the same pharmacologic activities as the corresponding bases. For many purposes it is preferable to administer the salts rather than the base compounds. Among the acid addition salts suitable for this purpose are salts such as the sulfate, phosphate, lactate, tartrate, maleate, citrate, hydrobromide and hydrochloride. Both the base compounds and the salts have the distinct advantage of possessing a relatively low order of toxicity.

The antidepressant activity of the compounds of formulae 1 and 1a and their acid addition salts with pharmaceutically acceptable salts is demonstrated in standard pharmacologic tests such as, for example, the tests described by F. Hafliger and V. Burckhart in "Psychopharmacological Agents", M. Gordon, Ed., Academic Press, New York and London, 1964, pp. 75 – 83.

More specifically, as noted in the latter reference the antidepressant properties of a compound may be demonstrated by its capacity to antagonize the depressant effects of reserpine. Furthermore, it is well documented that reserpine in animals produces a model depression which can be used for detecting antidepressant properties. Accordingly, the compounds of the present invention antagonize reserpine effects in mice at doses ranging from about 1 to 100 mg/kg. Several of the preferred compounds, for instance, 5-hydrazino-1,3-dihydropyrrolo[4,3,2-de]isoquinoline hydrochloride (Example 8) and 5-(isopropylidenehydrazino)-1,3-dihydropyrrolo[4,3,2-de]isoquinoline (Example 9), antagonize the effects of reserpine in mice at dose ranges from about 1 to 15 mg/kg.

When the compounds of formulae 1 and 1a are used as antidepressants in warm-blooded mammals, e.g. rats and mice, they may be used alone or in combination with pharmacologically acceptable carriers, the proportion of which is determined by the solubility and chemical nature of the compound, chosen route of administration and standard biological practice. For example, they are administered orally in solid form containing such excipients as starch, milk sugar, certain types of clay and so forth. They may also be administered orally in the form of solutions or they may be injected parenterally. For parenteral administration they may be used in the form of a sterile solution containing other solutes, for example, enough saline or glucose to make the solution isotonic.

The dosage of the present therapeutic agents will vary with the form of administration and the particular compound chosen. Furthermore, it will vary with the particular host under treatment. Generally, treatment is initiated with small dosages substantially less than the optimum dose of the compound. Thereafter, the dosage is increased by small increments until the optimum effect under the circumstance is reached. In general, the compounds of this invention are most desirably administered at a concentration level that will generally afford effective results without causing any harmful or deleterious side effects and preferably at a level that is in a range of from about 0.1 mg to about 100 mg per kilo per day, although as aforementioned variations will occur. However, a dosage level that is in the range of from about 0.5 mg to about 50 mg per kilo per day is most desirably employed in order to achieve effective results.

The antihypertensive effect of the compounds of formulae 1 and 1a and their acid addition salts is demonstrated also in standard tests, for example, in tests conducted in the spontaneously hypertensive rat such as described by R. Tabei, et al., clin. Pharmacol. Therap., 11, 269 (1970).

When the compounds of this invention are employed as antihypertensive agents they are formulated and administered in the same manner as described above for their use as antidepressant agents.

Process

The starting material for the compounds of this invention is the amide, 3,4-dihydropyrrolo[4,3,2-de]isoquinolin5(1H)-one (2). The preparation of this starting material is described in detail in our copending patent application of Philipp et al., Ser. No. 413,417 now U.S. Pat. No. 3,950,343 and entitled "Pyrroloisoquinoline Derivatives". Briefly a preferred preparation of this starting material involves treating 4-indolecarboxylic acid methyl ester, F. C. Uhle, J. Amer. Chem. Soc., 71, 761 (1949), with N-methylformanilide in the presence of phosphorus oxychloride according to the conditions of the Vilsmeier reaction to obtain 3-formylindole-4-carboxylic acid methyl ester, converting the latter compound to its corresponding oxime, catalytically reducing the oxime in the presence of hydrochloric acid and palladium on charcoal to obtain 3-(aminomethyl)indole-4-carboxylic acid methyl ester hydrochloride and finally treating the latter compound with sodium methoxide to give the desired starting material of formula 2.

Referring to the following flow diagram,

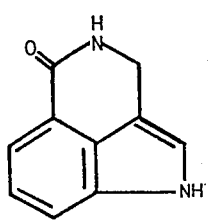

2

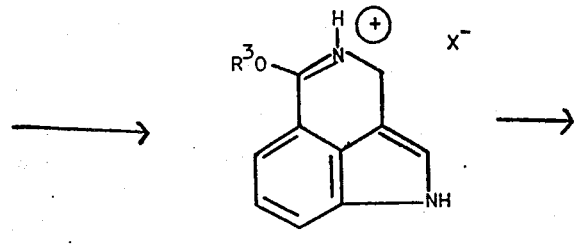

3

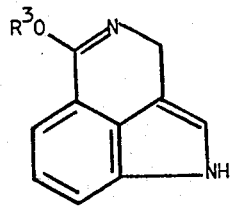

4

→ 1 → 1a the practice of the process of this invention first entails transforming the amide 2 by treatment with an appropriate amide O-alkylating reagent to its corresponding laction ether complex of formula 3 in which $R^3$ is lower alkyl and $X^-$ is the anion derived from the amide O-alkylating reagent. Although a number of reagents are available for this conversion, for example, triethyloxonium fluoroborate or dimethyl sulfate, see also, B. C. Challis and J. A. Challis in "The Chemistry of the Amides", J. Zabicky, Ed., Interscience Publishers, London, 1970, pp 734 – 754, the preferred reagent is triethyloxonium fluoroborate, giving the lactim ether complex of formula 3 in which $R^3$ is ethyl and X is $BF_4^-$. Thereafter, the lactim ether complex is decomposed with base to give the corresponding lactim ether of formula 4.

In a preferred embodiment for the conversion of the amide 2 to the lactim ether 4, said amide is treated with 1 to 1.5 molar equivalents of triethyloxonium fluoroborate in an inert solvent, for example, methylene dichloride, chloroform, ether and the like to give the lactim ether complex. The duration and temperature of this reaction is not critical, the reaction being conveniently performed at room temperature for periods of 12 to 24 hours. The substantially insoluble lactim ether complex is isolated readily by filtration and then subjected to the action of a base, for example, the alkali metal hydroxides or carbonates, preferably, sodium or potassium hydroxide, by suspending the complex and the base in a relatively polar solvent such as water, the lower alkanols or lower alkanones. Preferred polar solvents include water, methanol, acetone, ethanol or mixtures thereof.

The lactim ether of formula 4, obtained in the above described manner, is a key intermediate for the pyrroloisoquinolines of this invention.

Accordingly the lactim ether reacts with appropriate nucleophilic reagents; such as ammonia, primary amines, for example, methyl- or ethylamine or 3-(dimethylamino)propylamine, secondary amines, for example dimethyl- or dipropylamine, hydrazine or hydrazine derivatives, for example, methylhydrazine or 1,1-dimethylhydrazine, to yield the desired pyrroloisoquinolines of this invention which in certain cases are also intermediates transformable to other desired compounds of this invention.

Generally speaking the lactim ether 4 is treated with the appropriate nucleophilic reagent with or without the presence of an acid component. Preferably at least one equivalent of the acid component, with respect to the nucleophilic reagent, is employed, although the amount of acid component may range from 0.01 to 10 equivalents. The acid component is added separately to the reaction mixture or incorporated with the nucleophilic reagent in the form of an acid addition salt. Suitable acid components are the inorganic acids, hydrochloric acid, hydrobromic acid, phosphoric acid and the like and the organic acids, p-toluenesulfonic acid, citric acid, acetic acid and the like. In the case of the weaker nucleophiles the presence of the acid component is most desirable; however, the higher nucleophility of hyrazine and hydrazine derivatives allow the reaction of these agents with the lactim ether 4 to proceed without the presence of the acid component. The reaction is preferably carried out in an inert solvent, for example, methanol, ethanol, chloroform, methylene dichloride, dioxane and the like. For the purpose of this reaction it is not essential that the lactim ether be dissolved in the solvent; partial solubility of the lactim ether being quite suitable. Furthermore the reaction times and temperatures are not critical; practical times and temperatures for reacting the various nucleophiles are noted in the ensuing discussions of the reactions based on the particular nucleophile employed.

Alternatively, the lactim ether complex 3, for example, the hydrofluoroborate salt thereof, react with the nucleophilic reagents to yield the corresponding hydrofluoroborate salt of the pyrroloisoquinolines of formula 1. Since hydrofluoroborate salts are generally not considered salts derived from pharmaceutically acceptable acids, the hydrofluoroborate salt is then transformed into other salts, for example, the hydrochloride, sulfate, and the like, by standard methods, for example, by utilization of an anionic exchange resin.

When it is desired to prepare the compounds of formula 1 in which $R^1$ is amino, the lactim ether of formula 4 is reacted with ammonia or ammonium hydroxide preferably in the presence of at least one equivalent of an acid component, or reacted with an ammonium salt, for example, ammonium chloride, ammonium sulfate and the like. The duration and temperature of this reaction usually varies from 10 minutes to three hours and from 20° to 100°C. In practice it has been found convenient to effect the reaction in methanol using a reaction time of 30 minutes and a reaction temperature determined by the reflux temperature of the mixture.

Similarly, when it is desired to prepare the compounds of formula 1 in which $R^1$ is lower alkylamino, di(lower)alkylamino or di(lower)alkylamino(lower)-)alkylamino, the lactim ether is reacted with the appropriate amine, for example, methylamine, diethylamine or 3-(dimethylamino)propylamine, preferably in the presence of at least one equivalent of an acid component or reacted with an acid addition salt of the amine. The time needed to complete this reaction usually varies from about 2 to 24 hours at temperatures ranging from 20° to 100°C.

When it is desired to prepare the compounds of formula 1 in which $R^1$ is hydrazino, 2-(lower)alkylhydrazino and 2,2-di(lower)alkylhydrazino, the lactim ether is reacted with hydrazine or an appropriate hydrazino derivative, for example, methylhydrazine, 1,1-dimethylhydrazine, or reacted with an acid addition salt of hydrazine or the hydrazine derivative. As noted before the acid component can be omitted in the present reaction involving hydrazine or its derivatives without any substantial effect on the course of the reaction. The present reaction proceeds to completion usually over periods of 30 minutes to 48 hours at temperatures of 20° to 100°C. In practice reactions times of one to 18 hours at the reflux temperature of the mixture, using methanol or ethanol as the solvent, have been found to be convenient and efficacious.

When it is desired to prepare the pyrroloisoquinoline of formula 1 in which $R^1$ is isopropylidenehydrazino, the aforementioned compound of formula 1 in which $R^1$ is hydrazino is treated with acetone. This particular reaction proceeds quite facilely and the reaction time and temperature are not critical. Convenient conditions for this reaction include dissolving or suspending the pyrroloisoquinoline of formula 1 in acetone and subjecting the mixture to reflux for about 1 hour.

Finally the compounds of formula 1a in which $R^2$ is hydrogen or methyl are obtained by reacting the aforementioned compound of formula 1 in which $R^1$ is hydrazine with formic acid or acetic anhydride, respectively, at 0° – 100°C for 15 minutes to six hours with or without an inert solvent (see above). The compound of formula 1a in which $R^2$ is methyl is obtained also by reacting the lactim ether 4 with acetylhydrazine, preferably in an inert solvent such as methanol or ethanol.

The following examples illustrate further this invention.

EXAMPLE 1

3-Formylindole-4-carboxylic acid methyl ester

To a stirred mixture of N-methylformanilide (15.6 g) and phosphorus oxychloride (17.7 g) is added ethylene dichloride (75 g) followed by 4-indolecarboxylic acid methyl ester (17.5 g), described by F. C. Uhle, J. Amer. Chem. Soc., 71, 761 (1949). The reaction mixture is stirred at room temperature for 1½ hr., then at 45° – 50°C for 30 minutes more. The mixture is now poured into a solution of 75 g of sodium acetate in 150 ml of ice-water. More ethylene dichloride is added. The layers are separated and the organic phase is washed with water, dried ($Na_2SO_4$) and evaporated under reduced pressure. The brown residue is treated repeatedly with boiling water from which the title compound separates on cooling. The title compound has mp 135°C.

EXAMPLE 2

3-Formylindole-4-carboxylic acid methyl ester oxime

A mixture of 3-formyl-4-indolecarboxylic acid methyl ester (2.03 g), described in Example 1, 10 ml of a 5M aqueous solution of hydroxylamine hydrochloride, 10 ml of 5M aqueous sodium acetate and 20 ml of methanol is stirred at 45° – 55°C for 1 hour. The precipitate is collected and washed with cold water. Recrystallization from methanol-water gives the title compound, mp 178° – 179°C.

EXAMPLE 3

3-(Aminomethyl)indole-4-carboxylic Acid Methyl Ester

To 3-formylindole-4-carboxylic acid methyl ester oxime (1 g), described in Example 2, in 50 ml of methanol is added 5 ml of a saturated solution of HCl in methanol and 100 mg of 5% Pd/C. This mixture is stirred magnetically at room temperature in a hydrogen atmosphere until hydrogen uptake ceases. The catalyst is collected on a filter and the filtrate concentrated to dryness under reduced pressure. The resulting powder is dissolved in ethanol and precipitated out with ether to afford the hydrochloride salt of the title compound, nmr ($CDCl_3$) δ 4.05 (3H), 4.28 (2H), 7.00 – 8.00 (4H).

The present intermediate can be used in the process of the invention as an acid addition salt, for example, the above hydrochloride salt. If desired, the corresponding free base, $\nu_{max}^{CHCl_3}$ 1736 cm$^{-1}$, is obtained by treating an anhydrous methanol solution of the salt with an equivalent of sodium methoxide, followed by filtration and concentration of the solution.

EXAMPLE 4

3,4-Dihydropyrrolo[4,3,2-de]isoquinolin-5(1H)-one (2)

Preparation A

A mixture of 3-formylindole-4-carboxylic acid methyl ester oxime (1.6 g), described in Example 2 and platinum oxide (120 mg) in 60 ml of acetic acid is stirred in a hydrogen atmosphere for 16 hour. Removal of the catalyst and concentration of the solution affords an oily residue [the acetic acid addition salt of 3-(aminomethyl)indole-4-carboxylic acid methyl ester]. The oil is suspended in water. The mixture is rendered alkaline with a 10% aqueous solution of NaOH. The solid is collected, triturated with 30% acetone in benzene and recrystallized from ethanol to afford the title compound, mp 232°–234°, $\nu_{max}^{CHCl_3}$ 1668 cm$^{-1}$.

Preparation B

Sodium metal (19.2 g) is dissolved in absolute methanol (1 l.) with ice-water cooling. To the clear solution is added a solution of 3-(aminomethyl)indole-4-carboxylic acid methyl ester hydrochloride (102.7 g), described in Example 3, in absolute methanol (1 l.). The addition is done in portions within a few minutes. After stirring for 1.5 hour at room temperature the solution is concentrated to near dryness and ice cold water (250 ml) is added to the crystalline residue. The precipitate is collected, washed with cold water and dried to give the title compound, mp 232° – 234°C, identical to the product of Preparation A of this example.

EXAMPLE 5

5-Ethoxy-1,3-dihydropyrrolo[4,3,2-de]isoquinoline (4)

3,4-Dihydropyrrolo[4,3,2-de]isoquinolin-5(1H)-one (8.6 g), described in Example 4, is added in one portion to a solution of 12 g of triethyloxonium fluoroborate [H.-L. Pan and T. L. Fletcher, J. Org. Chem., 27, 3639 (1962)] in 500 ml dry methylene chloride. The suspension is stirred for 24 hours. The solid is collected and washed with a little methylene chloride and then ether to give 5-ethoxy-1,3-dihydropyrrolo[4,3,2-de]isoquinoline hydrofluoroborate, mp 233° – 234°C, $\nu_{max}^{nujol}$ 3380, 3280, 1645, 1605, 1594, 1540 and 1512 cm$^{-1}$.

The latter compound (7.7 g) is suspended in methanol-water (1:1, 200 ml). The mixture is cooled in an ice bath and rendered alkaline with aqueous sodium bicarbonate. The solid is collected, washed well with water, dried to giive the title compound, mp 155° – 156°C, $\nu_{max}^{nujol}$ 3140, 1636, 1606, 1588, and 1500 cm$^{-1}$, nmr (DMSO-$d_6$) δ 1.37 (t, J=7, 3H), 4.34 (q, J=7, 2H), 5.23 (2H), 7.20 (m. 4H), 11.20 (broad s, 1H).

EXAMPLE 6

5-Amino-1,3-dihydropyrrolo[4,3,2-de]isoquinoline (1, $R^1 = NH_2$)

To a suspension of 5-ethoxy-1,3-dihydropyrrolo[4,3,2-de]isoquinoline (200 mg, 1 mmole), described in Example 5, in ethanol (2 ml), aqueous ammonium hydroxide (25%, 0.5 ml, 1.4 mmole) is added followed by 2.3 N HCl in ethanol (0.5 ml). The mixture is heated at reflux for 0.5 hour, then ether is added and the light green crystalline precipitate collected to give the hydrochloride salt of the title compound, 5-amino-1,3-dihydropyrrol[4,3,2-de]isoquinoline hydrochloride, mp 227° – 228°C.

The hydrochloride salt is converted to its corresponding free base in the following manner. The salt is dissolved in water. The solution is rendered alkaline with 5% NaOH solution. The solid is collected, washed with water and dried to give the title compound, mp 233° – 235°C, $\nu_{max}^{nujol}$ 3150, 1665, 1635, 1605, 1590, 1540 and 1520 cm$^{-1}$.

In the same manner but replacing ammonium hydroxide with an equivalent amount of methylamine (40% aqueous solution) or diethylamine (30% aqueous solution),5-(methylamino)-1,3-dihydropyrrolo[4,3,2- de]isoquinoline and 5-(diethylamino)-1,3-dihydropyrrolo[4,3,2-de]isoquinoline are obtained, respectively.

EXAMPLE 7

5-[3-(Dimethylamino)propylamino]-1,3-dihydropyrrolo[4,3,2-de]isoquinoline [1, R$^1$ = NH(CH$_3$)$_2$N(CH$_2$)$_3$]

A mixture of 5-ethoxy-1,3-dihydropyrrolo[4,3,2-de]isoquinoline (5 g, 25 mmoles), described in Example 5, ethanol (50 ml), 3-(dimethylamino)propylamine (2.7 g, 26.4 mmoles) and conc. HCl (12.5 ml, 29 mmoles) in 50 ml of ethanol is heated at reflux for 7 hours. Some ethanol is removed by distillation, then ether and saturated HCl in ethanol (2 ml) is added. The precipitate is collected. Recrystallization for ethanol-ethyl acetate (a small amount of HCl in ethanol being added) gives the hydrochloride salt of the title compound, mp 289° – 290°C.

Conversion of the salt as described in Example 6 to its corresponding free base gives the title compound, nmr (D$_2$O) δ 1.90 (2H), 2.48 (6H), 2.68 (2H), 3.12 (2H), 4.28 (2H), 6.96 (2H), 7.45 (1H).

In the same manner but replacing 3-(dimethylamino)propylamine with an equivalent amount of 2-(diethylamino)ethylamine, 5-[2-(diethylamino)ethylamino]-1,3-dihydropyrrolo[4,3,2-de]isoquinoline is obtained.

EXAMPLE 8

5-Hydrazino-1,3-dihydropyrrolo[4,3,2-de]isoquinoline (1, R$^1$ = NH$_2$NH)

A solution of 5-ethoxy-1,3-dihydropyrrolo[4,3,2-de]isoquinoline (10.0 g), described in Example 5, in methanol (100 ml) is combined with a solution of hydrazine hydrate (3 g) in methanol (150 ml). After boiling overnight the mixture is concentrated to half of its original volume and diluted with ether. The resulting precipitate is collected to give the title compound, mp 188° – 189°C, $\nu_{max}^{nujol}$ 3370, 3325, 3150, 1628, 1583, 1540 and 1510 cm$^{-1}$.

The corresponding hydrochloride salt of the title compound is prepared by treating the title compound in methanol with an excess of hydrogen chloride in ether. The hydrochloride salt has mp 310° – 312°C (decomp. beginning at > 300°C) after recrystallization from methanol.

In the same manner but replacing hydrazine hydrate with an equivalent amount of methylhydrazine or 1,1-dimethylhydrazine, 5-(2-methylhydrazino)-1,3-dihydropyrrolo[4,3,2-de]isoquinoline and 5-(2,2-dimethylhydrazino)-1,3-dihydropyrrolo[4,3,2-de]isoquinoline are prepared respectively.

Similarly, treatment of equimolar amounts of 5-ethoxy-1,3-dihydropyrrolo[4,3,2-de]isoquinoline hydrofluoroborate, described in Example 5, and hydrazine hydrate in methanol gives 5-hydrazino-1,3-dihydropyrrolo[4,3,2-de]isoquinoline hydrofluoroborate, mp 263° – 265°C.

EXAMPLE 9

5-(Isopropylidenehydrazino)-1,3-dihydropyrrolo[4,3,2-de]isoquinoline (1, R$^1$ = (CH$_3$)$_2$C=NNH)

5-Hydrazino-1,3-dihydropyrrolo[4,3,2-de]isoquinoline (4.5 g), described in Example 8, is boiled in acetone (ca. 50 ml) for 10 minutes. The reaction mixture is treated with charcoal, filtered and concentrated. Addition of ether-hexane gives a precipitate. The precipitate is recrystallized from benzenemethanol-ether to give the title compound, mp 200° – 201°C, $\nu_{max}^{nujol}$ 3450, 3100, 1625, 1565, 1540 and 1510 cm$^{-1}$.

EXAMPLE 10

4,6-Dihydropyrrolo[4,3,2-de]-s-triazolo[3,4-a]isoquinoline (1a, R$^2$ = H)

5-Hydrazino-1,3-dihydropyrrolo[4,3,2-de]isoquinoline hydrofluoroborate (300 mg), described in Example 8, in formic acid (98%, 4 ml) is heated at 100°C for 2 hours. The mixture is then poured into a saturated sodium bicarbonate solution. The precipitate is collected to give the title compound, mp 248° – 249°C, nmr (DMSO-d$_6$) δ 5.65 (2H), 7.3 (4H), 8.5 (1H), 11.3 (1H).

EXAMPLE 11

4,6-Dihydro-8-methylpyrrolo[4,3,2-de]-s-triazolo[3,4-a]isoquinoline (1a, R$^2$ = CH$_3$)

5-Hydrazino-1,3-dihydropyrrolo[4,3,2-de]isoquinoline hydrochloride (50 mg), described in Example 8, is heated at reflux with 3 ml of acetic anhydride for 2 hours. The mixture is cooled and then poured into a saturated solution of sodium bicarbonate. The resulting precipitate is collected and then dissolved in methanol. This solution is rendered acidic by the addition of HCl in ether. The mixture is treated with charcoal and concentrated to give the title compound.

Alternatively the title compound is prepared as follows. A suspension of 5-ethoxy-1,3-dihydropyrrolo[4,3,2-de]isoquinoline (9.0 g) in dry ethanol (140 ml) is treated with acetylhydrazine (5.0 g). The mixture is heated at reflux for 2 days. Ethanol is partially removed by distillation and ether-hexane added. The solid is collected from methanol to give the title compound.

The title compound has mp > 300°C (dec.), $\nu_{max}^{nujol}$ 2900 cm$^{-1}$, $\lambda_{max}^{MeOH}$ 328 nm (ε = 8190), 307nm (ε = 8490), 241 nm (ε = 29600), 234 nm (ε = 28800).

We claim:
1. A compound of the formula

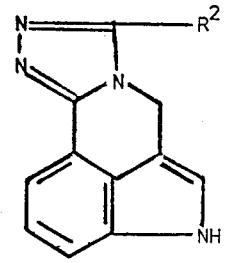

in which R$^2$ is hydrogen or methyl.
2. 4,6-Dihydropyrrolo[4,3,2-de]-s-triazolo[3,4-a]isoquinoline, as claimed in claim 1.
3. 4,6-Dihydro-8-methylpyrrolo[4,3,2-de]-s-triazolo[3,4-a]isoquinoline, as claimed in claim 1.

* * * * *